United States Patent [19]

Di Gianfilippo et al.

[11] Patent Number: 4,467,844

[45] Date of Patent: Aug. 28, 1984

[54] FLOW MONITORING METHOD AND APPARATUS

[75] Inventors: Aleandro Di Gianfilippo, Arlington Heights; Alan A. Figler, Algonquin, both of Ill.

[73] Assignee: Baxter Travenol Laboratories, Inc., Deerfield, Ill.

[21] Appl. No.: 391,758

[22] Filed: Jun. 24, 1982

[51] Int. Cl.³ ............................................. B65B 3/04
[52] U.S. Cl. ......................................... 141/1; 141/83; 141/94; 177/50; 604/65; 340/613
[58] Field of Search ................... 141/1, 83, 9, 99–107, 141/237–248, 94–96, 367, 368, 351–362; 177/50, 1, 70, 80, 121, 137, 164, 210 R, 211; 222/39, 52, 77; 340/606, 613; 73/296; 604/65, 66, 67, DIG. 12, DIG. 13

[56] References Cited

U.S. PATENT DOCUMENTS 3,749,285  7/1973  Latham, Jr. ............................ 222/58
3,985,266 10/1976  Wright, Jr. ............................ 222/22
4,137,915  2/1979  Kamen ................................... 604/65
4,345,628  8/1982  Campbell ............................... 141/83

*Primary Examiner*—Houston S. Bell, Jr.
*Attorney, Agent, or Firm*—Robert A. Benziger; Paul C. Flattery

[57] ABSTRACT

The present invention provides an economical quick and accurate method and apparatus for transferring and monitoring a preselected amount of fluid from a fluid source container to a receiving container. The method and apparatus monitors the flow rate of the fluid to be transferred by measuring the weight change of the receiving container per unit time.

A weight sensor monitors the weight of the receiving container at various time intervals. The weight information received by the control module at the various time intervals is compared to each other and to predetermined values for the detection of no flow, low flow or high flow conditions.

24 Claims, 2 Drawing Figures

FLOW MONITORING METHOD AND APPARATUS

BACKGROUND OF THE INVENTION

The present invention pertains to a fluid transfer and monitoring method and device for delivering a predetermined amount of fluid. More particularly, the present invention pertains to a method and device for the direct measurement and control of the precise amount of fluid transferred.

Hospitals, pharmacies and laboratories are required to deliver a predetermined amount of fluid to be analyzed, to fill unit dosage syringes, medical containers or other receptacles with identical, repeatable quantities. It is important that a high degree of accuracy as well as cleanliness and sterility be maintained in these operations. Further, a high productivity rate is desirable along with the high standards of accuracy, cleanliness and sterility to efficiently use personnel, and minimize cost without sacrificing quality.

A known manual apparatus and process for transferring fluids utilizes a solution transfer system including a receiving container and a Y-transfer set. The Y-transfer set includes two separate tubes, each having an end attached to a common juncture by which solutions delivered through the tubes will pass through the juncture into the receiving container. The other end of one tube of the set is attached to one solution container and the other end of the other tube of the set is attached to another solution container. The desired volume of each solution being transferred to the receiving container is controlled by a clamp placed on each tube. The solutions may be allowed to flow into the receiving container by gravity flow. However, it has been found to be useful to transfer the solutions under the influence of a vacuum applied to the receiving container. When the receiving container is a flexible plastic container, the vacuum is created in a vacuum chamber into which the container is placed.

It has been known in the past that to ensure sterility during the transfer of solutions, the process should be performed under a laminar flow hood. Laminar flow hoods are used for reducing the risk of airborne contamination of such solutions. These units operate by taking room air and passing it through a pre-filter to remove gross contaminates, such as dust and lint. The air is then compressed and channeled through a bacterial retentive filter in the hood in a laminar flow fashion. The purified air flows out over the entire work surface of the hood in parallel lines at a uniform velocity. The bacterial retentive type of filter is designed to remove all bacteria from the air being filtered.

Transferring solutions under a laminar flow hood aids in preventing airborne contamination, but it is relatively cumbersome and expensive and would not be useful for eliminating any other source of contamination, such as contamination caused by handling. When using a hood the operator may inadvertently perform the work at the end or outside of the hood and not within the recommended space, at least six (6) inches within the hood, which insures the benefits of the air being purified. Time must be taken and care must be exercised to maintain a direct open path between the filter and the compounding area. Solution bottles and other nonsterile objects cannot be placed at the back of the hood work area next to the filter because these objects could contaminate everything downstream and disrupt the laminar flow pattern of the purified air. Also, in using a laminar flow hood, it is necessary routinely to clean the work surface of the hood before any compounding is performed.

Thus, the prior art manual or semi-manual apparatuses and processes discussed above are disadvantageous due to their inefficiency for filling large numbers of containers encompassing extensive number of hand operations which are labor intensive, time consuming and can be error prone.

Modern machines are capable of transferring fluids at high speeds with some degree of accuracy. However, the methods employed in these machines to monitor the delivery of a predetermined amount of fluid require actual measurement of the flow speed of the fluid. In measuring the flow speed of fluids, special purpose dedicated monitoring devices such as air detectors, ultrasonic transducers, doppler transmit/receive devices are employed. These devices only measure the fluid flow indirectly and therefore are vulnerable to inaccuracies as well as not providing reproducible results. This, of course, is a major drawback when it is required to deliver a repeatable, accurate predetermined amount of fluid quickly and efficiently.

Another known method of attaining accuracy in the transfer of a predetermined amount of fluid is by a volumetric chamber. This method requires a volume chamber which is costly to manufacture due to the requirement of precise tolerances to maintain an exact volume therein. The method is also slow and interrupts the laminar flow of the fluid to be transferred. Further, air in the volume chamber can effect the determination of the amount transferred.

The method and device of the present invention overcomes the above-discussed disadvantages. Further, the present invention provides for the actual monitoring of the fluid being transferred to achieve a quick, accurate, reproducible transfer of fluids. The present invention therefore provides for high productivity while maintaining high standards for accuracy and repeatability.

A process and apparatus that can utilize the hereindescribed invention is disclosed and claimed in co-pending U.S. application Ser. No. 391,759 filed concurrently herewith, in the names of Carl Miller and Lawrence R. Hogan for HIGH SPEED BULK COMPOUNDER which application is assigned to the assignee of the present invention and is incorporated herein by reference.

As disclosed therein, quick and accurate delivery of fluids is accomplished by sequentially controlled peristaltic pumps operatively connected between the solution containers and a receiving container. A controller receives data from an operator on the amount, by volume, of each solution to be compounded and its specific gravity. The comparison of this data to the weight sensed in a collection container permits the controller to sequentially operate the pumps. The controller is also able to monitor various process conditions. Failure to achieve these process conditions results in an automatic shutdown of the operation.

SUMMARY OF THE INVENTION

In accordance with the present invention, a method and apparatus is provided for transferring and monitoring a predetermined amount of fluid from at least one fluid source containing a fluid to a fluid receiving container. Positive motive means, in the form of a peristaltic pump for example, or the like, is operatively connected between the fluid sources and fluid receiving container to effect fluid transfer. The method and apparatus monitors the flow rate of the fluid by measuring the weight change of the fluid receiving container, as will be discussed more fully below.

The flow rate of a fluid transferred to a receiving container can be expressed as the weight change of the container times the specific gravity of the fluid divided by the time period. Since the specific gravity and the time periods can be defined as constants, the flow rate can be expressed as being directly proportional to the weight change. Therefore, by monitoring the weight change of the container and comparing it to predetermined operating conditions, it is possible accurately and precisely to deliver a predetermined amount of fluid and to monitor the fluid transfer for malfunctions.

The apparatus of the present invention includes detecting means which can be a load cell, strain gauge or the like, for detecting a first weight of the receiving container at a first instant of time and a second weight of the container at a second instant of time later than said first instant of time. Comparing means of the apparatus then compares the first and second weights which actuates an alarm when the second weight is not greater than the first weight thereby indicating lack of fluid flow to the receiving container.

The apparatus further includes a motive means sensor that initiates the detection of the first and second weights when the operation of the motive means is sensed. Also, the comparing means include a further comparing means for comparing the first and second weights against a predetermined weight change. The further comparing means actuates a low flow indicator or a high flow indicator when the weight change between the first and second weights is either less than or greater than the predetermined weight change thereby indicating a low or high fluid flow condition.

The method of the present invention includes detecting a first weight of the receiving container at a first instant of time and detecting a second weight of the receiving container at a second instant of time. The first and second weights are then compared and an alarm is activated if the second weight is not greater than the first weight thereby indicating lack of fluid flow from the fluid sources to the receiving container.

The method further includes initiating weight detecting attendant to the sensing of the operation of transfer or motive means. Further, the method includes comparing the first and second weights to a predetermined weight change and activating either a low flow or high flow indicator attendant to the difference between said first and second weights being less than or greater than the predetermined weight change.

The apparatus and method of the present invention provide for fast, efficient and precise monitoring of fluid transfer to achieve an accurate and reproducible predetermined amount of fluid to be transferred. Further, the invention is less costly to manufacture and is readily adaptable to a variety of fluid transfer systems.

DETAILED DESCRIPTION

Figure 1:
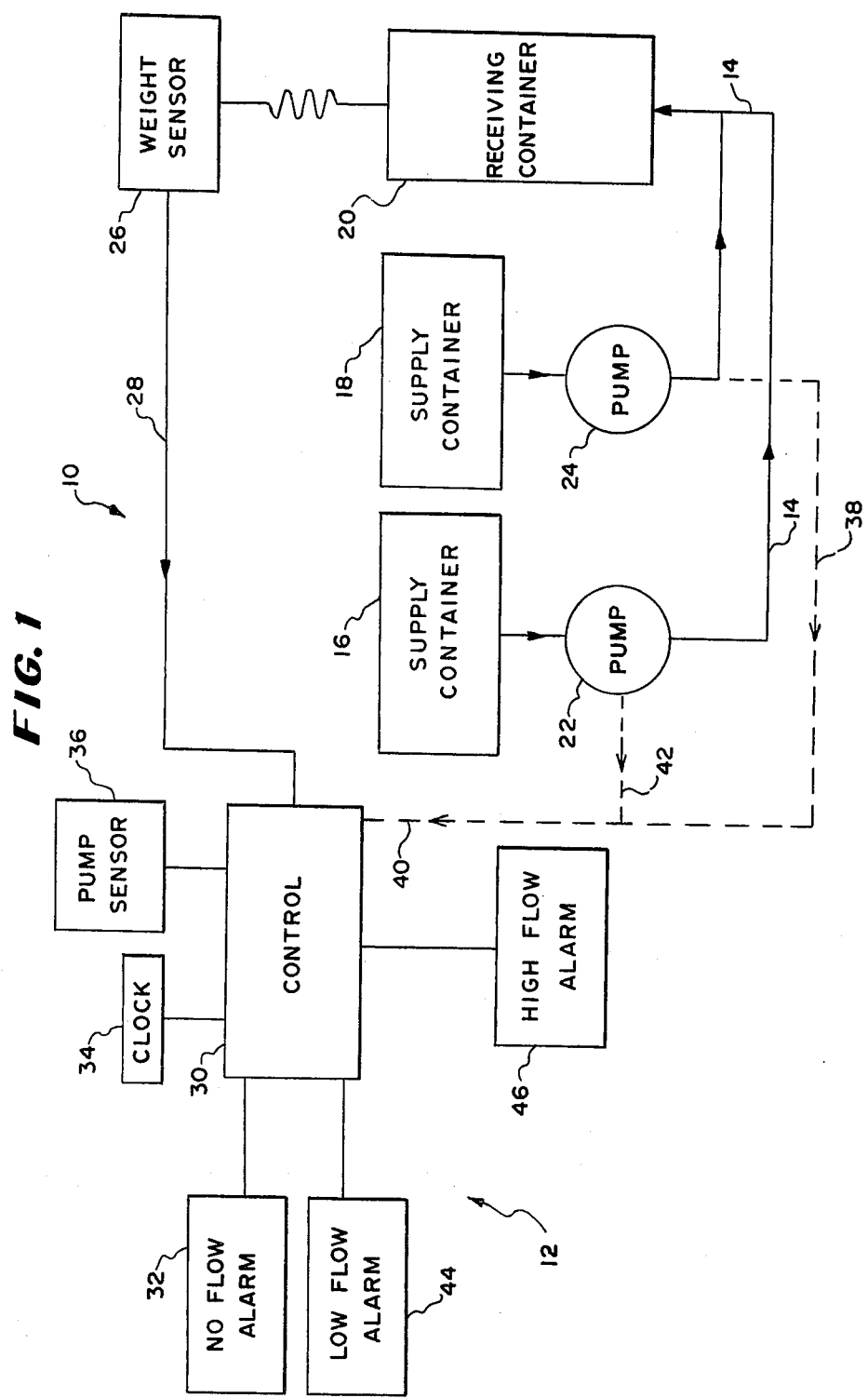
FIG. 1 is a block diagram configured in accordance with the present invention.

Referring now to FIG. 1 there is shown diagramatically, an apparatus 10 which incorporates the present invention of a fluid flow monitor generally shown at reference numeral 12. The apparatus 10 transfers fluid, through a transfer medium 14, such as flexible tubing or the like, from supply containers 16 and 18 to a collection or receiving container 20. Fluid transfer is effected by a pair of pumps 22 and 24 operatively connected between each supply container and the receiving container 20. The pumps 22 and 24 can be of any positive fluid pumping type, but are preferably peristaltic pumps for use in sterile applications. The apparatus 10 is illustrated and described as having two supply containers; however, one supply container or a plurality of containers can also be used in conjunction with the present invention.

The device 12 monitors the flow rate of the fluid being transferred from the supply containers 16 and 18 to the receiving container 20. The device 12 includes alarms for alerting personnel of conditions of no flow, low flow or high flow in the system thereby indicating malfunctions, such as, empty supply containers, broken transfer tubing, line blockage, malfunctioning of pumps or simultaneous pump operation.

Fluid flow monitoring for delivering a predetermined amount of fluid is accomplished in the present invention by the comparison of fluid weights taken at preselected time intervals. This can be explained by the expression of flow rate equalling weight change times a constant (specific gravity divided by the time interval). This mode of monitoring flow rates is more accurate and more economical than the indirect measurement of fluid speed by ultrasonic transducers and the like or by the slow and costly volume chamber method.

In accordance with the above described premise a weight sensor or detector 26 such as a load cell, strain gauge or the like detects the weight of the receiving container and relays this information through a line 28 to a control module 30. The control module 30 includes means for comparing each pair of consecutive weights taken at succeeding times, to determine if there has been a weight gain from the preceeding detected weight. If there has not been a weight gain an alarm 32 is sounded indicating lack of fluid flow from the supply containers 16 and 18 to the receiving container 20 representing empty supply containers, breach of the tube or the like. A delay means, down counter or clock 34 is utilized to select the weight at the desired preselected times for use with the comparing means.

The device 12 further includes a sensor 36 which is operatively coupled through lines 38, 40 and 42 to pumps 22 and 24. The sensor 36, which can be of the electrical variety, initiates the detection of weight at the preselected intervals and senses the operation of more than one pump. The device 12 also includes further comparing means for comparing the difference between two consecutive weights detected at successive times to a predetermined weight change for the selected time period involved. If the difference in weight between the two consecutive weights is less than the predetermined weight change an alarm 44 is sounded indicating a low fluid flow condition which could mean a crimped tube, a malfunctioning pump or the like. In the event the weight change exceeds the predetermined weight change, an alarm 46 is sounded indicating a high fluid flow condition which could mean a malfunctioning pump, simultaneous operation of pumps or the like.

Figure 2:
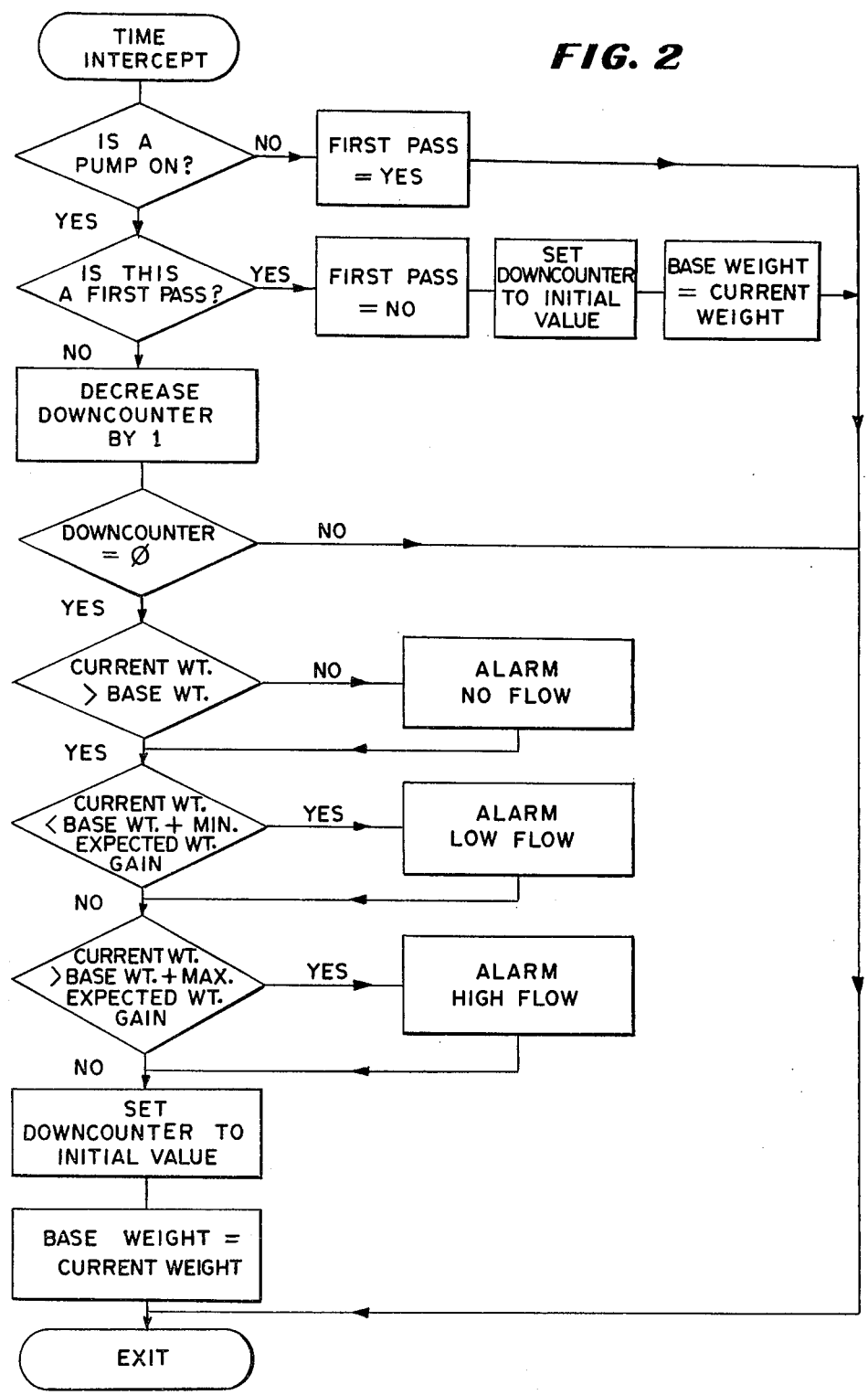
FIG. 2 is a flow chart configured in accordance with the present invention.

Turning now to FIG. 2 there is shown a flow diagram for carrying out the method of operation of the control module 30. The sensor 36, at a time period controlled by the clock 34, determines if a pump is on, if no pump is on the module 30 sets a first pass counter to yes. This continues until the operation of a pump is sensed, at which time the module 30 sets the first pass counter to no, initializes a down counter to a preselected value and recodes a first base weight. At each succeeding time period the module 30 decreases the down counter by one unit until the down counter equals zero.

Once the down counter equals zero the next period actuates the detection of the second or current weight on line 28 and the module 30 compares it to the first base weight. If the current weight is not greater than the base weight an alarm is actuated to indicate a no flow condition. If the current weight is greater than the base weight, the down counter is then reset and the current weight is set equal to the base weight and the cycle is reinitiated.

Prior to resetting the down counter, the method can further incorporate checks for low flow and high flow conditions in addition to or in place of no flow. This can be accomplished by comparing the weight change between the base and current weights to a desired predetermined weight change or range of changes. If the actual weight change is less than a first predetermined weight change a low flow alarm is actuated and if a actual weight change is greater than the preselected weight change a high flow alarm is actuated. In terms of the flow diagram of FIG. 2, the module 30 initiates the comparison of the current weight to the total of the base weight plus the minimum expected weight gain during the time period. If the current weight is less than the total a low flow alarm is actuated, if the current weight is not less than that total the module 30 initiates a comparison between the current and the total of the base weight plus the maximum expected weight gain during the time period. If the current weight is greater than that total, a high flow alarm is actuated and if not then the down counter is reset and the base weight is set equal to the current weight.

It has been found that precisely to monitor and transfer the predetermined amounts of fluid from the supply containers to the receiving container the speed of the fluid should be decreased for the final portion of the fluid to be delivered. The decreased rate allows for a more precise monitoring of the fluid flow and therefore a more precise determination of the final weight in the receiving container 20. This is accomplished by transferring the majority of the fluid to be transferred at a first high speed and transferring the final portion of the fluid to be transferred at a second slower speed, preferably in pulses, to accurately obtain the desired preselected weight. Of course, the operation of the present invention takes into account the change in pump speeds and corresponding flow rates.

Modifications and variations of the present invention are possible in light of the above teachings. It is therefore to be understood that within the scope of the appended claims the invention may be practiced, otherwise than as specifically described.

What is claimed and desired to be secured by Letters Patent of the United States is:

1. A fluid transfer and monitoring apparatus for delivering a predetermined amount of fluid from at least one fluid source adapted to contain a fluid, to a fluid receiving container adapted to receive fluid from said fluid source, through motive means operatively adapted to transfer said fluid from said fluid source to said receiving container, the improvement comprising:
    means for detecting a first base weight of said fluid receiving container at a first instant of time and a second weight of said fluid receiving container at a second instant of time later than said first instant of time;
    means for comparing said first and second weights; and
    alarm means responsive to said comparison means for initiating an alarm when said second weight is not greater than said first weight thereby indicating lack of fluid flow from said fluid source to said receiving container.

2. The apparatus of defined in claim 1 including:
    sensing means for sensing the operation of said motive means; and
    said detecting means initiating detecting said first base weight and said second weight responsive to said sensing means sensing the operation of said motive means.

3. The apparatus as defined in claim 2 wherein said means for detecting includes weight sensing means for sensing the weight of said receiving container.

4. The apparatus as defined in claim 3 wherein said weight sensing means is a load cell.

5. The apparatus as defined in claim 3 wherein said weight sensing means is a strain gauge.

6. The apparatus as defined in claim 3 wherein:
    said means for comparing includes further comparing means for comparing said first and second weights against a predetermined weight change; and
    said alarm means including low flow indicator means for indicating low flow when said weight change between said first and second weights is less than said predetermined weight change.

7. The apparatus as defined in claim 6 wherein said alarm means further includes high flow indicator means for indicating high flow when said weight change between said first and second weights is greater than said predetermined weight change.

8. The apparatus as defined in claim 7 including delay means for determining said second instant of time later than said first instant of time.

9. The apparatus as defined in claim 3 wherein:
    said means for comparing include further comparing means for comparing a correlate of said first and second weights against a correlate of a predetermined weight change; and
    said alarm means including low flow indicator means for indicating low flow when said correlate of said weight change between said first and second weights is less than said correlate of said predetermined weight change.

10. The apparatus as defined in claim 9 wherein said alarm means further include high flow indicator means for indicating high flow when said correlate of said weight change between said first and second weights is greater than said correlate of said predetermined weight change.

11. The apparatus as defined in claim 7 wherein:
    said motive means is operated at a first operational speed for delivering a portion of said predetermined weight; and said motive means is operated at a second operational speed, slower than said first operational speed, for delivering a final portion of said predetermined weight.

12. The apparatus as defined in claim 11 wherein said second operational speed delivers small amounts of fluid in pulses for the final portion of said predetermined weight to accurately obtain said predetermined weight.

13. The apparatus as defined in claim 1, 2 or 6 wherein there is provided a plurality of solution sources.

14. A method for precisely monitoring fluid transfer of a predetermined amount from at least one fluid source, to a fluid receiving container, by motive means, comprising:

detecting a first base weight of said receiving container at a first instant of time and detecting a second weight of said receiving container at a second instant of time later than said first instant of time;

comparing said first and second weights; and activating an alarm when said second weight is not greater than said first weight, thereby indicating lack of fluid flow from said fluid source to said receiving container.

15. The method as defined in claim 14 further including:

delivering said at least one fluid by operating said motive means;

sensing the operation of said motive means; and initiating detection of said first base weight and said second weight responsive to the sensing of the operation of said motive means.

16. The method as defined in claim 15 wherein detecting said first and second weights is accomplished by a load cell.

17. The method as defined in claim 15 wherein detecting said first and second weights is accomplished by a strain gauge.

18. The method as defined in claim 15 including:

comparing said first and second weights against a predetermined weight change; and activating an alarm for a low flow condition when said weight change between said first and second weights is less than said predetermined weight change.

19. The method as defined in claim 18 further including activating an alarm for a high flow condition when said weight change between said first and second weights is greater than said predetermined weight change.

20. The method as defined in claim 17 including: comparing a correlate of said first and second weights against a correlate of a predetermined weight change; and activating an alarm for a low flow condition when said correlate of said weight change between said first and second weights is less than said correlate of said predetermined weight change.

21. The method as defined in claim 20 further including activating an alarm for a high flow condition when said correlate of said weight change between said first and second weights is greater than said correlate of said predetermined weight change.

22. The method as defined in claim 19 further including:

operating said motive means at a first operational speed for delivering a portion of said predetermined weight; and operating said motive means at a second operational speed, slower than said first operational speed, for delivering a final portion of said predetermined weight.

23. The method as defined in claim 22 wherein operating said motive means at said second operational speed includes delivering small amounts of said fluid in pulses for the final portion of said predetermined weight to accurately obtain said predetermined weight.

24. The method as defined in claim 14, 15, 19 or 23 including transferring fluids to said receiving container from a plurality of fluid sources.

* * * * *